United States Patent
Kouchi et al.

(10) Patent No.: US 7,371,214 B2
(45) Date of Patent: May 13, 2008

(54) VITAL SIGN DISPLAY DEVICE AND METHOD THEREOF

(75) Inventors: Kenji Kouchi, Toyonaka (JP); Ryuji Nagai, Takatsuki (JP); Shinya Nagata, Kobe (JP)

(73) Assignee: Dainippon Sumitomo Pharma Co., Ltd. (JP)

(*) Notice: Subject to any disclaimer, the term of this patent is extended or adjusted under 35 U.S.C. 154(b) by 0 days.

(21) Appl. No.: 10/525,747

(22) PCT Filed: Aug. 26, 2003

(86) PCT No.: PCT/JP03/10734

§ 371 (c)(1),
(2), (4) Date: Feb. 25, 2005

(87) PCT Pub. No.: WO2004/019779

PCT Pub. Date: Mar. 11, 2004

(65) Prior Publication Data

US 2006/0074321 A1 Apr. 6, 2006

(30) Foreign Application Priority Data

Aug. 27, 2002 (JP) ............... 2002-246627

(51) Int. Cl.
*A61B 5/00* (2006.01)
(52) U.S. Cl. ...................... 600/300; 128/905
(58) Field of Classification Search ........ 600/300–301; 128/920, 905
See application file for complete search history.

(56) References Cited

U.S. PATENT DOCUMENTS 5,262,944 A * 11/1993 Weisner et al. ............. 600/300
5,718,235 A 2/1998 Golosarsky et al.

FOREIGN PATENT DOCUMENTS

| JP | 51-000787 | 1/1976 |
|---|---|---|
| JP | 55-23615 | 6/1980 |
| JP | 64-7783 | 10/1989 |
| JP | 04-504966 | 9/1992 |
| JP | 04-352939 | 12/1992 |
| JP | 05-154117 | 6/1993 |
| JP | 06-261871 | 9/1994 |
| JP | 07-313478 | 12/1995 |
| JP | 10-505515 | 6/1998 |
| JP | 2000-107146 | 4/2000 |
| JP | 2003-000559 | 1/2003 |

OTHER PUBLICATIONS

Chinese Official Action (Including translation), mailed Dec. 1, 2006, for corresponding Chinese patent application.

* cited by examiner

*Primary Examiner*—Max F. Hindenburg
*Assistant Examiner*—Michael C Astorino
(74) *Attorney, Agent, or Firm*—Sheridan Ross P.C.; Jason H. Vick

(57) ABSTRACT

A vital sign display device and method which allows a vital sign to be checked easily is provided. A vital sign item name is displayed at the center of a circle radar (50). The circle part of the circle radar (50) is colored in gray, for example, at the beginning of the measurement. An indication point moves clockwise in the circle radar (50) as the measurement time proceeds. Green is displayed while VPCs (ventricular premature contractions) do not occur, and red is displayed when VPCs occur.

35 Claims, 11 Drawing Sheets

VITAL SIGN DISPLAY DEVICE AND METHOD THEREOF

CROSS-REFERENCE TO RELATED APPLICATIONS

The present application claims the benefit of patent application No. 2002-246627, filed in Japan on Aug. 27, 2002, and the subject matter of which is hereby incorporated herein by reference.

BACKGROUND OF THE INVENTION

1. Field of the Invention

The present invention relates to a device and a method for displaying a vital sign and more particularly for facilitating the check of biological signal.

2. Description of the Related Art

In the technical field of displaying biological information such as blood pressure or electrocardiogram, some techniques have been developed to allow the biological information to be easily checked. There is a technique for displaying an event mark at a time position corresponding to electrocardiographic data during an attack on a trend graph of an electrocardiographic parameter such as heart rate or ST level (see Patent Document 1, for example). Patent Document 1: JP-A-Hei 4-352939 (FIG. 8).

According to the technique, it is possible to determine when attacks occurred, for example, with the event marks. That is, according to the existing technique, it is possible to obtain information about when abnormal values of biological information appeared.

In a medical site, however, a technique to allow for easy visual acquisition of more comprehensive biological information in addition to the determination of individual abnormal values may be demanded.

SUMMARY OF THE INVENTION

In one aspect, the invention provides a vital sign display device and method thereof that are capable of facilitating check of biological information. The invention includes the following:

(1) A vital sign display device in accordance with the present invention for displaying a vital sign, comprises means for obtaining a biological signal, means for determining whether living body condition represented by the biological signal is abnormal or not, which is based on the obtained biological signal, and means for displaying a vital sign obtained from the biological signal, that allows to discriminate whether the condition is abnormal or not, which is based on the determination results from the determining means, wherein the vital sign is arranged in time series that allows to provide history of the vital sign.

The user who utilizes the results outputted by the vital sign displaying means can easily understand that the living body is in normal condition or abnormal condition. Since the vital sign is successively displayed in time series so that the user can understand the history of the vital sign, for example, the user can easily understand information regarding timing in which the patient's abnormal condition occurred and frequency of occurrence of the abnormal condition.

(3) A vital sign display device in accordance with the present invention for displaying a vital sign, comprises means for displaying a vital sign, obtained from the biological signal or signal generated from the biological signal, that allows to discriminate whether living body condition represented by the signal is abnormal or not, wherein the vital sign is arranged in time series that allows to provide history of the vital sign.

The user who utilizes the results outputted by the vital sign displaying means can easily understand that the living body is in normal condition or abnormal condition. Since the vital sign is successively displayed in measurement sequence so that the user can understand the history of the vital sign, for example, the user can easily understand information regarding timing in which the patient's abnormal condition occurred and frequency of occurrence of the abnormal condition.

(4) The device in accordance with the present invention is characterized in that the vital sign is displayed so as to follow a circular shape according to time series of the vital sign.

The device can, to some extent, prevent display area for the vital sign from extending or spreading according to the passage of measurement time. Therefore, the user who utilizes the results outputted by the vital sign displaying means can easily make a visual identification for a general trend of the vital sign.

(5) A vital sign display device in accordance with the present invention for displaying a vital sign, comprises means for obtaining a biological signal, means for determining whether living body condition represented by the biological signal is abnormal or not, which is based on the obtained biological signal, and means for displaying a vital sign obtained from the biological signal, that allows to discriminate whether the condition is abnormal or not based on the determination results from the determining means, wherein the display is executed by moving a display object in the direction to draw a circular shape according to time series of the vital sign.

The user who utilizes the results outputted by the vital sign displaying means can easily understand that the living body is in normal condition or abnormal condition.

(6) The device in accordance with the present invention, is characterized in that the device further comprises means for selecting display style, and the display style selecting means selects length of entire display period corresponding to display area for the vital sign by correlating with measurement period of the vital sign.

The length of display time corresponding to display area can be adjusted in accordance with the measurement period of the vital sign.

(7) The device in accordance with the present invention, is characterized in that the device comprises means for displaying item name of vital sign, and the vital sign item name displaying means displays the item name by relating the item name to the displayed vital sign.

The user who utilizes the results outputted by the vital sign displaying means can easily understand that which of the vital sign items is related to the condition of vital sign.

(8) The device in accordance with the present invention, is characterized in that the display style of vital sign is changed to another style when the abnormal condition occurs.

The user who utilizes the results outputted by the vital sign displaying means can easily make a visual identification for an abnormal condition of the living body.

(9) The device in accordance with the present invention, is characterized in that the vital sign comprises at least an item of VPC (ventricular premature contraction), HR (heart rate), QT interval, or $SpO_2$ value (oxygen saturation in blood).

The user who utilizes the results outputted by the vital sign displaying means can easily make a visual identification for the vital sign of the VPC, HR, QT interval, or $SpO_2$ value.

(13) A vital sign displayed object in accordance with the present invention, representing a vital sign, is characterized in that the vital sign displayed object represents a vital sign obtained from a biological signal, that allows to discriminate whether living body condition represented by the biological signal is abnormal or not, wherein the vital sign is arranged in time series that allows to provide history of the vital sign.

The user who utilizes the results outputted by the vital sign displaying means can easily understand that the living body is in normal condition or abnormal condition. Since the vital sign is successively displayed in time series so that the user can understand the history of the vital sign, for example, the user can easily understand information regarding timing in which the patient's abnormal condition occurred and frequency of occurrence of the abnormal condition.

The followings are definitions of the terms.

"Biological signal" is a concept that includes any biological information or information about the pathologic conditions. The "biological signal" includes individual values (parameters) that represent biological information and information represented based on a plurality of pieces of biological information.

"Vital sign" is a concept that includes anything which is displayed based on a biological signal to make it possible to determine whether a condition of a living body represented by the biological signal is abnormal or not. For example, the concept includes changing the shape or color of displayed object to make it possible to determine whether a condition of a living body is normal or abnormal in addition to specific codes, symbols, marks, figures and letters which make it possible to determine whether a condition of a living body is normal or abnormal.

"Vital sign item name" is a concept that includes names representing matters relating to biological information. For example, the concept includes the names of parameters which represent matters relating to biological information, the names of pathologic conditions and the names of diagnosis.

"Normal" is a concept that includes a right (ordinary) state and a non-abnormal state in addition to a case where it can be determined that there is no disorder. For example, the concept includes a case where a value representing biological information is in a range within which the value falls when a living body is in good condition or determined as not abnormal by a specific determination method.

"Abnormal" is a concept that includes a non-right (non-ordinary) state and a non-normal state in addition to a case where biological information indicates that there is a disorder. For example, the concept includes a case where a value representing biological information is out of a range within which the value falls when a living body is in good condition or determined as abnormal by a specific determination method.

"To determine whether a living body is in an abnormal condition" includes to determine the presence or absence (or the degree) of abnormality, to determine the presence or absence (or the degree) of normality, or to determine whether the subject matter is normal or abnormal (,or to determine the degree of normality or abnormality of the subject matter).

"Circular shape" is a concept that includes any shape around which one can make a circuit. For example, the concept includes a loop shape, ring shape, circle shape, round shape, oval shape, doughnut shape, annular shape, and polygonal shape formed by straight lines, curves or a combination of straight lines and curves.

The features of the present invention can be described broadly as set forth above. The structures and characteristics of the present invention will be apparent from the following detailed description of the invention together with those features, effects, and drawings.

DESCRIPTION OF THE PREFERRED EMBODIMENTS

A vital sign circle radar device as an embodiment of the "vital sign display device" will be described below. The embodiments illustrates process for displaying vital sign circle radar based on the patient ECG data etc. According to the following embodiments, for example, the user of the device can intuitively and easily obtain information regarding timing in which the patient's abnormal condition occurred and frequency of occurrence of the abnormal condition during transferring the patient.

An overview of the embodiments, hardware configurations of devices, embodiments and structures corresponding to the terms in claims, and details of embodiments will be described below.

Table of Contents for the Embodiments

1. Outline of Vital Sign Circle Radar to be Displayed
2. Hardware Configurations of Devices
3. Embodiments
4. Example of Vital Sign Circle Radar to be Displayed
5. Vital Sign Circle Radar Creation Process
6. Effects of Embodiment
7. Other Functions of the Vital Sign Circle Radar Device
8. Other Embodiments

1. Outline of Vital Sign Circle Radar to be Displayed

A vital sign circle radar is a displayed image representing a vital sign of a patient obtained from an electrocardiogram or the like. A vital sign circle radar device 100 for performing the display will be described later. This device is suitable for the use in emergency situations or in ambulances and hospitals. In this embodiment, description will be made taking as an example a case where it is used by an emergency medical technicians in an ambulance carrying a patient.

FIG. 1 is a schematic view of examples of a displayed vital sign circle radar. FIGS. 1A, 1B, 1C and 1D are images of a circle radar 50 in time-series order displayed on a display screen 14 to indicate the presence or absence of occurrence of "ventricular premature contractions (VPCs)" as one of vital signs. One cycle of the circle radar 50 corresponds to a measurement period of 20 minutes.

Figure 1A:
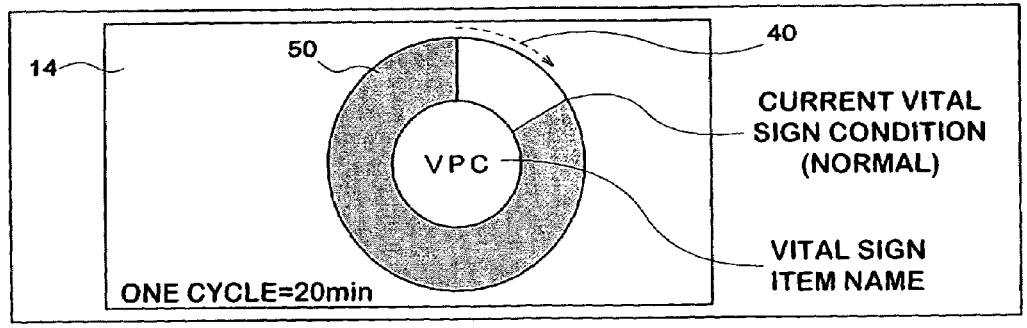
FIGS. 1A, 1B, 1C, and 1D illustrate schematic view of displayed vital sign circle radar according to an embodiment of the present invention.

As indicated by an arrow 40 in FIG. 1A, an indication point moves clockwise in the circle radar 50 as the measurement time increases (a displaying object is moved in direction to draw a circular shape according to time series of the vital sign). The vital sign item name is displayed at the center of the circle radar 50. The circle part (ring part or doughnut ring part) of the circle radar 50 is colored in gray at the beginning of the measurement. After the start of the measurement, it is determined whether there is an abnormality in the vital sign at every heartbeat and the indication point moves clockwise (see the arrow 40 in FIG. 1A). Then, the color of the ring part is changed depending on the result of the abnormality determination. That is, the circle radar 50 is displayed in such a manner that it can be determined whether the vital sign is normal or abnormal. More specifically, green is displayed while VPCs do not occur (normal), and red is displayed when VPCs occur (abnormal) (the display style is changed). In the drawing, the periods of time in which VPCs did not occur are shown in white and the periods of time in which VPCs occurred are shown in black for the sake of convenience. Since normal and abnormal conditions are displayed in colors different from the gray of the circle part, the progress of the measurement and the current display position can be visually recognized with ease. More specifically, FIG. 1A shows that the vital sign (VPC) is normal at the moment.

Figure 1B:
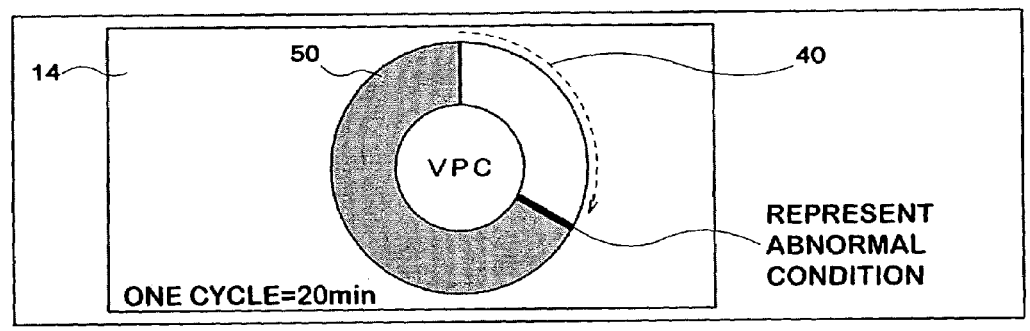

FIG. 1B shows an example of the screen on the display screen 14 at the time when VPCs occur. When a VPC occurs in a period in the measurement time, the indication point corresponding to the period is shown (painted) in red as shown in FIG. 1B. More specifically, FIG. 1B shows that the vital sign (VPC) is abnormal at the moment.

Figure 1C:
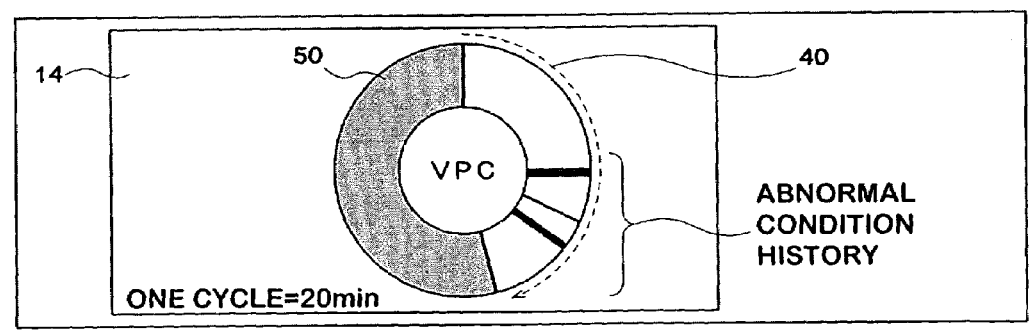

FIG. 1C shows an example of the state of the display screen 14 after some more measurement time has passed from the moment when the display screen 14 was in the state shown in FIG. 1B. As shown in the drawing, the periods in which VPCs occurred are displayed in red in the circle radar 50. The user of the device can know the history of abnormal conditions (history of the vital sign), that is, when or how often VPCs (ventricular premature contractions) occurred, by viewing the red sections. More specifically, FIG. 1C shows that the vital sign (VPC) indicates that VPCs are occurring (abnormal) at the moment and that several abnormal conditions have occurred in the past. The width of the sections displayed in red represents the length of time for which the abnormal condition continued.

Figure 1D:
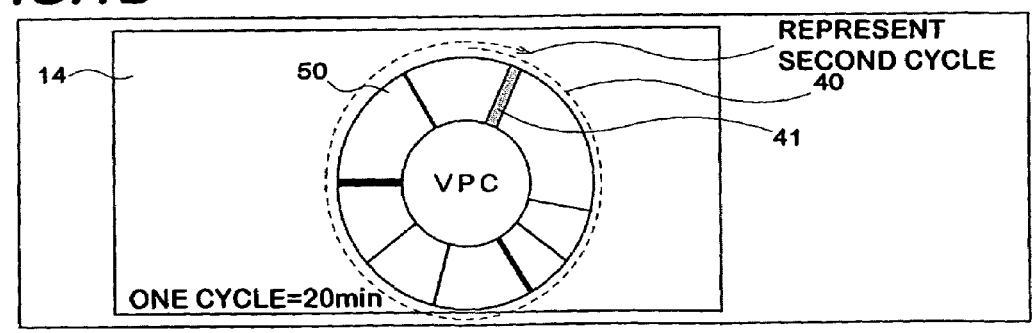

FIG. 1D shows an example of the state of the display screen 14 after the measurement time has exceeded twenty minutes. When the measurement time exceeds twenty minutes, the indication point in the circle radar 50 moves more than one full turn. Thus, abnormality determination is performed in the same manner as in the first cycle with a gray section with a prescribed width after the indication point (see the reference numeral 41 in FIG. 1D), and new information is overwritten on (deletes) the old information displayed during the first cycle. More specifically, FIG. 1D shows that the vital sign (VPC) indicates that VPCs are not occurring at the moment (normal condition), that the measurement time has exceeded twenty minutes (in the second or more cycle), and that several abnormal conditions occurred in the past twenty minutes.

The shape and color of the vital sign circle radar 50 and the colors for indicating normal and abnormal conditions are illustrative and can be changed by means known to those skilled in the art.

The arrow 40 in FIG. 1 is shown to explain the movement of the indication point and thus is not displayed on the display screen 14 in reality. However, the arrow 40 (or a mark similar to the arrow 40) may be displayed on the display screen 14 to indicate the moving direction or the display position of the indication point clearly.

2. Hardware Configurations of Devices

Figure 2:
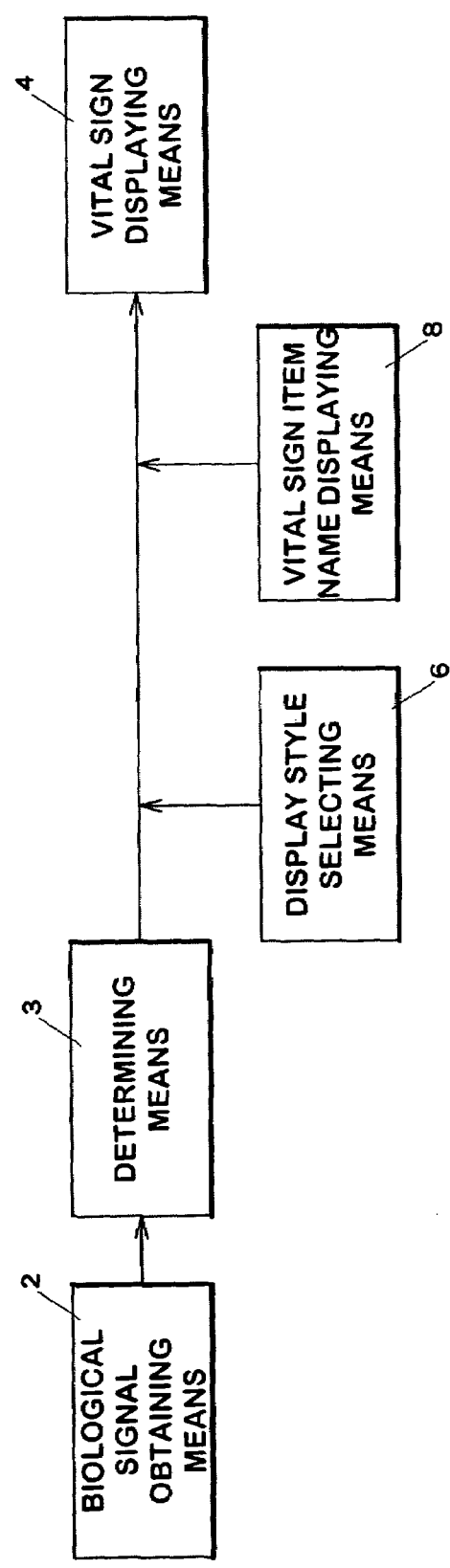
FIG. 2 illustrates a function block diagram of a vital sign circle radar device according to an embodiment.

FIG. 2 illustrates a function block diagram of a vital sign circle radar device 100. The vital sign circle radar device 100 includes biological signal obtaining means 2, determining means 3, vital sign displaying means 4, display style selecting means 6, and vital sign item name displaying means 8.

The biological signal obtaining means 2 obtains biological signal. The determining means 3 determines whether the biological signal represents a normal condition or an abnormal condition. The vital sign displaying means 4 displays the vital sign that displays the determination results as a vital sign circle radar. The display style selecting means 6 selects display style of the vital sign circle radar. The vital sign item name displaying means 8 displays item name of the vital sign by relating the item name to the vital sign circle radar.

Figure 3:
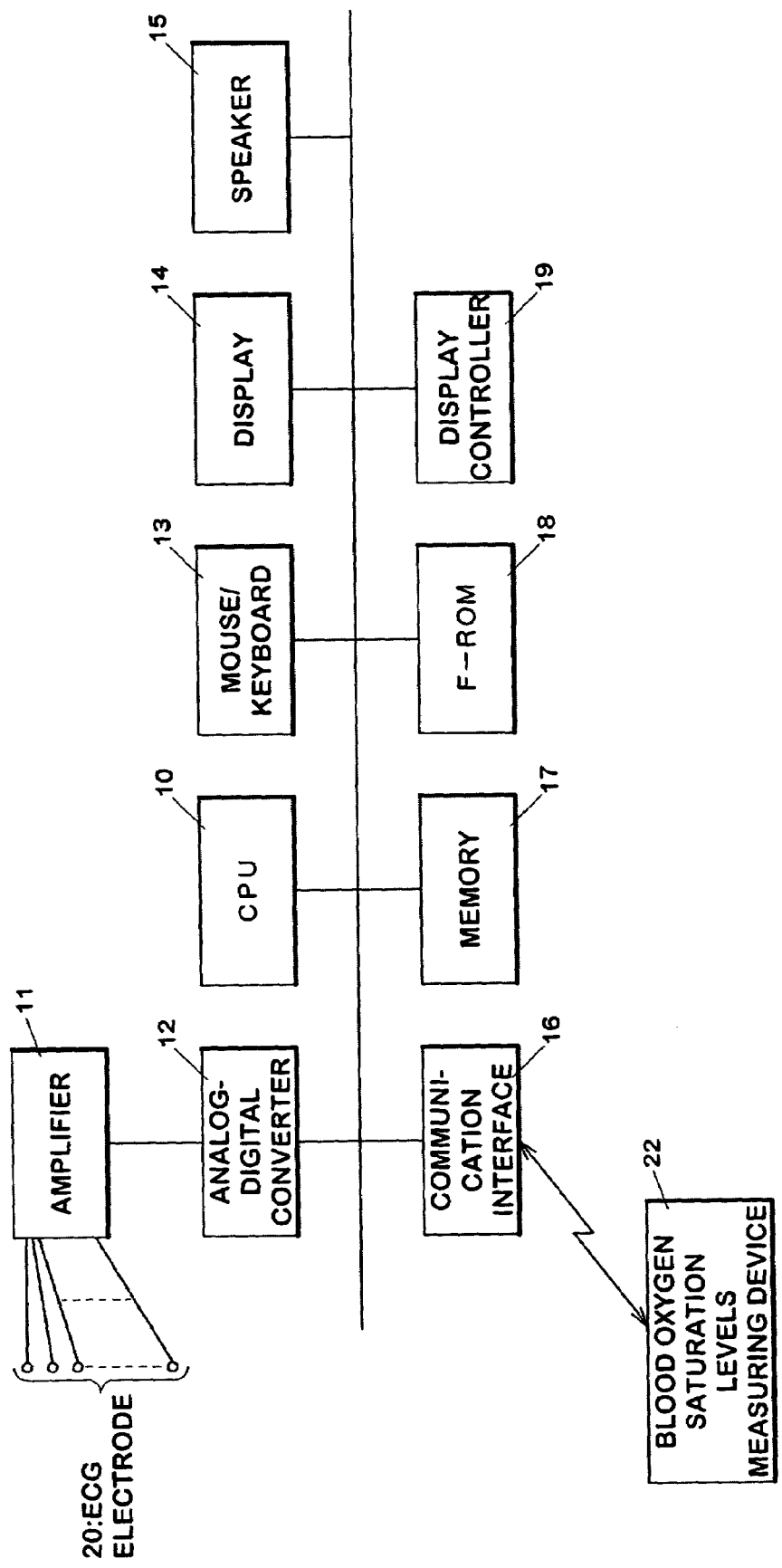
FIG. 3 illustrates a hardware configuration example for the vital sign circle radar device according to an embodiment.

FIG. 3 illustrates a hardware configuration example of the vital sign circle radar device 100 shown in FIG. 2 by use of a central processing unit (CPU). The vital sign circle radar device 100 includes CPU 10, amplifier 11, analog-digital converter 12, mouse/keyboard 13, display 14 (display device), speaker 15, communication interface 16, memory 17, Flash-ROM 18 (which corresponds to a rewritable read-only memory device from which recorded data can be electrically erased (e.g. the flash-memory), and will be described as "F-ROM 18"), display controller 19, and ECG electrodes 20 (biological signal detector).

The ECG electrodes 20 are used for measuring a patient's heart's electric current. The amplifier 11 amplifies the heart's electrical current obtained through ECG electrodes 20. The CPU 10 controls operations of the vital sign circle radar device 100, executes a process that converts data obtained from the heart's electric current to ECG data for displaying an ECG, and executes a process that generates a vital sign circle radar. The F-ROM 18 stores a computer program for controlling the vital sign circle radar device 100. The memory 17 acts as a storage area for data processing performed by the CPU 10. Operation information generated via operations of the mouse/keyboard 13 or the display controller 19 is inputted to the CPU 10, and the CPU 10 generates display information and sound information for the display 14 and the speaker 15 to output.

The vital sign circle radar device 100 is connected to device 22 for measuring blood oxygen saturation level (or biological signal detection device) via communication interface 16. The blood oxygen saturation level measuring device 22 is a device for measuring $SpO_2$ value of patient. In the embodiments, as an example of the communication interface 16, RS-232C etc. is utilized.

In the embodiments, examples of operating systems (OS) for the vital sign circle radar device 100 are Microsoft's Windows™ XP, NT, 2000, 98SE, ME, or CE. In alternative embodiments, the functions of the vital sign circle radar device 100 are accomplished with hardware logic (not shown) without the use of a CPU. The hardware configuration or CPU configuration can be modified by well-known techniques by those skilled in the art.

The "ECG" described in the embodiments is obtained by measuring electrical potential difference on the heart between two points on the patient's body. Therefore, the terms "ECG measurement" etc. used herein include the operations of measuring the heart's electrical potential etc.

3. Embodiments

The "vital sign display device" includes any device that displays vital sign. For example, the "vital sign display device" corresponds to vital sign circle radar device 100 illustrated in FIG. 3 as an embodiment. The "biological signal obtaining means" includes any means that has a function for obtaining biological signal. In the embodiments, the biological signal obtaining means corresponds to CPU 10 of the vital sign circle radar device 100 that executes a process of step S609 in FIG. 6. The "biological signal" includes any biological signal. In the embodiments, the "biological signal" corresponds to an identified value data or $SpO_2$ value at step S609 in FIG. 6.

The "determining means" includes any means that has a function for determining whether living body condition represented by the biological signal is abnormal or not based on the obtained biological signal. In the embodiments, the determining means corresponds to CPU 10 that executes processes of step S611 and S613 in FIG. 6.

The "vital sign displaying means" includes any means that has a function for displaying the vital sign. In the embodiments, the vital sign displaying means corresponds to CPU 10 that executes processes of step S615 and S617, or step S619 and S621 in FIG. 6. The "display style selecting means" includes any means that has a function for selecting display style. In the embodiments, the display style selecting means corresponds to CPU 10 that executes processes of setting display time for one lap of circle radar 50 at step S605 in FIG. 6. The "vital sign item name displaying means" includes any means that has a function for displaying item name of the vital sign. In the embodiments, the vital sign item name displaying means corresponds to CPU 10 that executes process of step S607 in FIG. 6.

4. Example of Vital Sign Circle Radar to be Displayed

An example of the vital sign circle radar to be displayed will be described. The vital sign circle radar creation process will be described in the next section.

Figure 4:
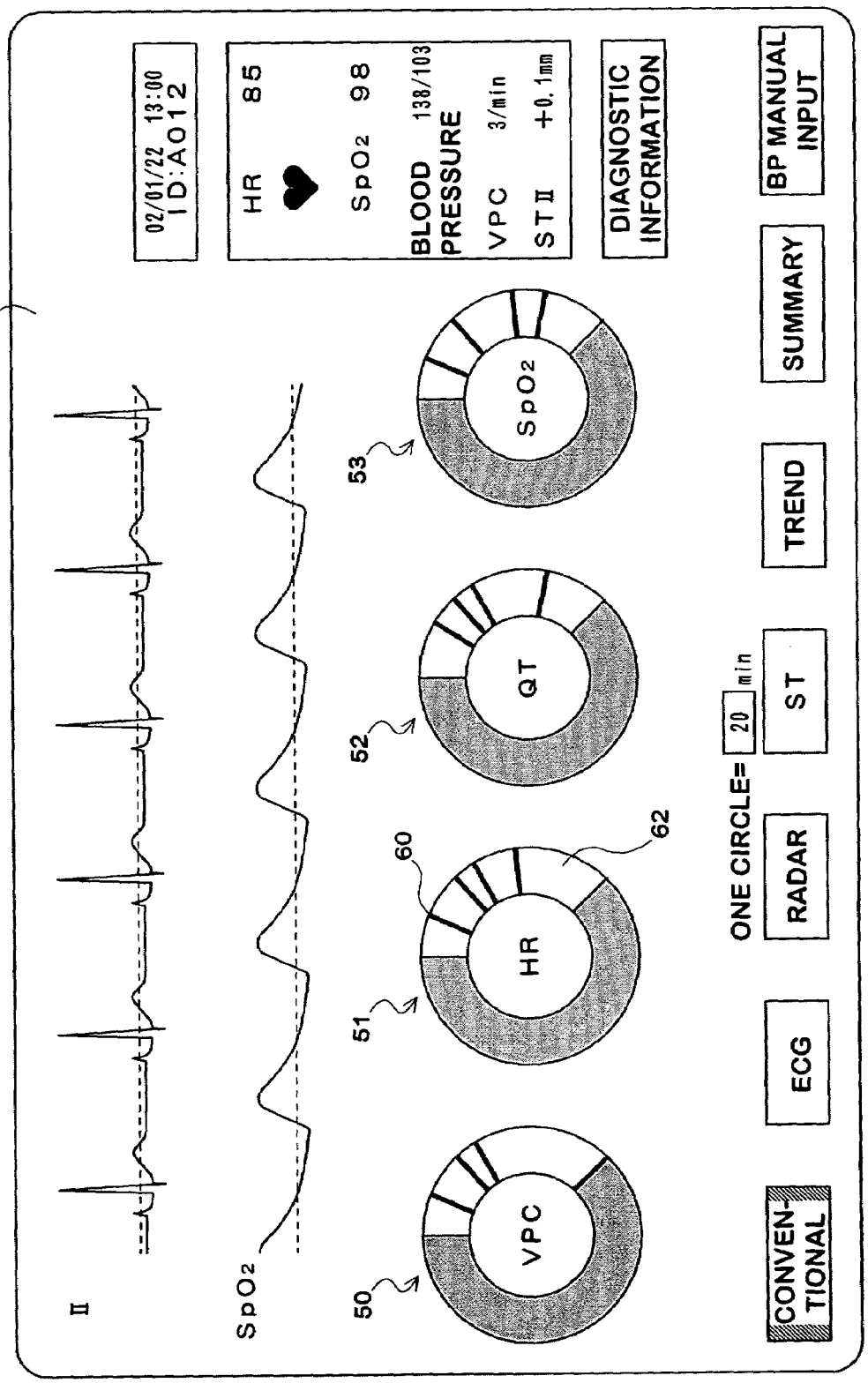
FIG. 4 illustrates a screen example of vital sign circle radar according to an embodiment.

FIG. 4 shows an example of the screen displayed by a vital sign circle radar creation process performed by the CPU 10.

As shown in the drawing, a vital sign circle radar 50 for VPC (ventricular premature contraction), a vital sign circle radar 51 for heart rate (HR), vital sign circle radar 52 for QT (QT interval), and a vital sign circle radar 53 for $SpO_2$ value are displayed on the display screen 14. In this embodiment, at least one of the vital sign circle radars for VPC, HR, QT and $SpO_2$ selected in advance by the user is displayed.

By each vital sign circle radar, the status of a vital sign is displayed as described in the section "1. Outline of Vital Sign Circle Radar to be Displayed." More specifically, an indication point moves in each vital sign circle radar as the measurement of a biological signal proceeds, and, when the living body is in an abnormal condition (the biological signal is showing an abnormal value), an abnormality indicator 60 (red) is displayed as the vital sign. When the living body is in a normal condition (the biological signal is showing a normal value), a normality indicator 62 (green) is displayed as the vital sign.

The electrocardiogram of the lead II as a representative lead, the trend of $SpO_2$ value obtained from a blood oxygen saturation level measuring device 22, and so on are also displayed on the display screen 14. The electrocardiogram and the trend of $SpO_2$ value can be displayed in a different style depending on the selection of the user. An electrocardiogram of another lead may be displayed or the display may be omitted. In this embodiment, a lead in which the amplitude is large is automatically selected and displayed as a representative lead.

Although VPC, HR, QT, and $SpO_2$ are shown as vital sign items to be selected by the user in this embodiment, the present invention is not limited thereto. The vital sign items to be employed can be changed by means known to those skilled in the art. For example, only a vital sign circle radar for VPC may be displayed, or vital sign circle radars for VPC and $SpO_2$ value may be displayed. Alternatively, a circle radar for an item other than the above four vital sign items (abnormal ST elevation, for example) may be displayed.

By the display of the vital sign circle radar as described above, the user of the vital sign circle radar device 100 can obtain information about when and how often abnormalities of a biological signal occurred intuitively and easily.

5. Vital Sign Circle Radar Creation Process 5-1. Precondition for Vital Sign Circle Radar Creation Process As a precondition for the vital sign circle radar creation process, the CPU 10 of the vital sign circle radar device 100 obtains 12-lead electrocardiograms via ECG electrodes 20 attached to the patient's body and an amplifier 11 and extracts an electrocardiographic waveform and the identified value (recognized value) data of the electrocardiographic waveform. The 12-lead electrocardiograms are twelve-pattern electrocardiograms which are obtained from several to dozen electrodes attached to a living body. The identified value data are used to determine the abnormality of a biological signal in this embodiment. The $SpO_2$ value is measured by the blood oxygen saturation level measuring device 22.

Figure 6:
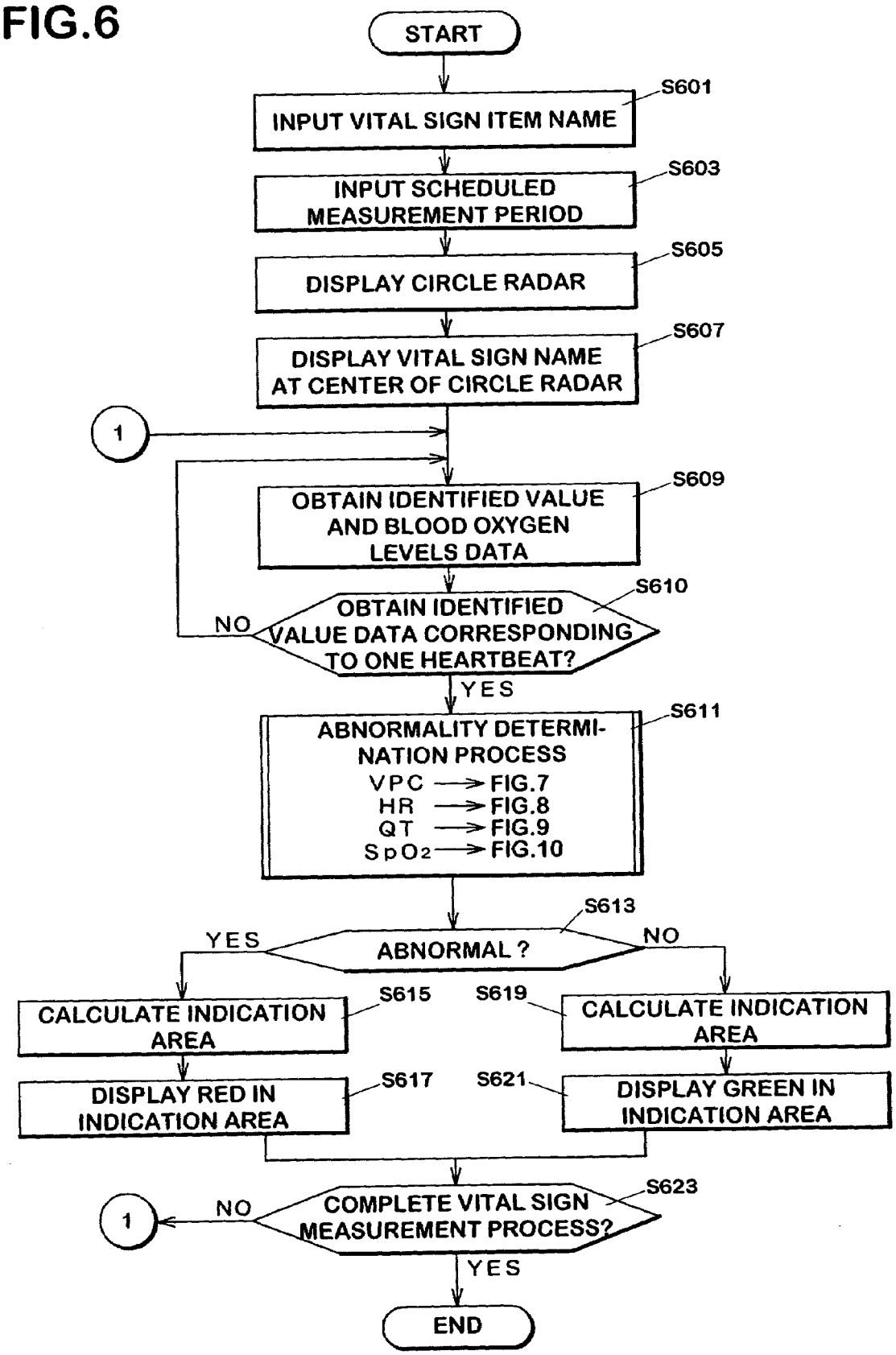
FIG. 6 illustrates a program flowchart for process that creates a vital sign circle radar according to an embodiment.

The flowchart in FIG. 6 shows that the CPU 10 performs the processes of receiving the recognized value data and the $SpO_2$ value and displaying a vital sign circle radar based on them.

Figure 5:
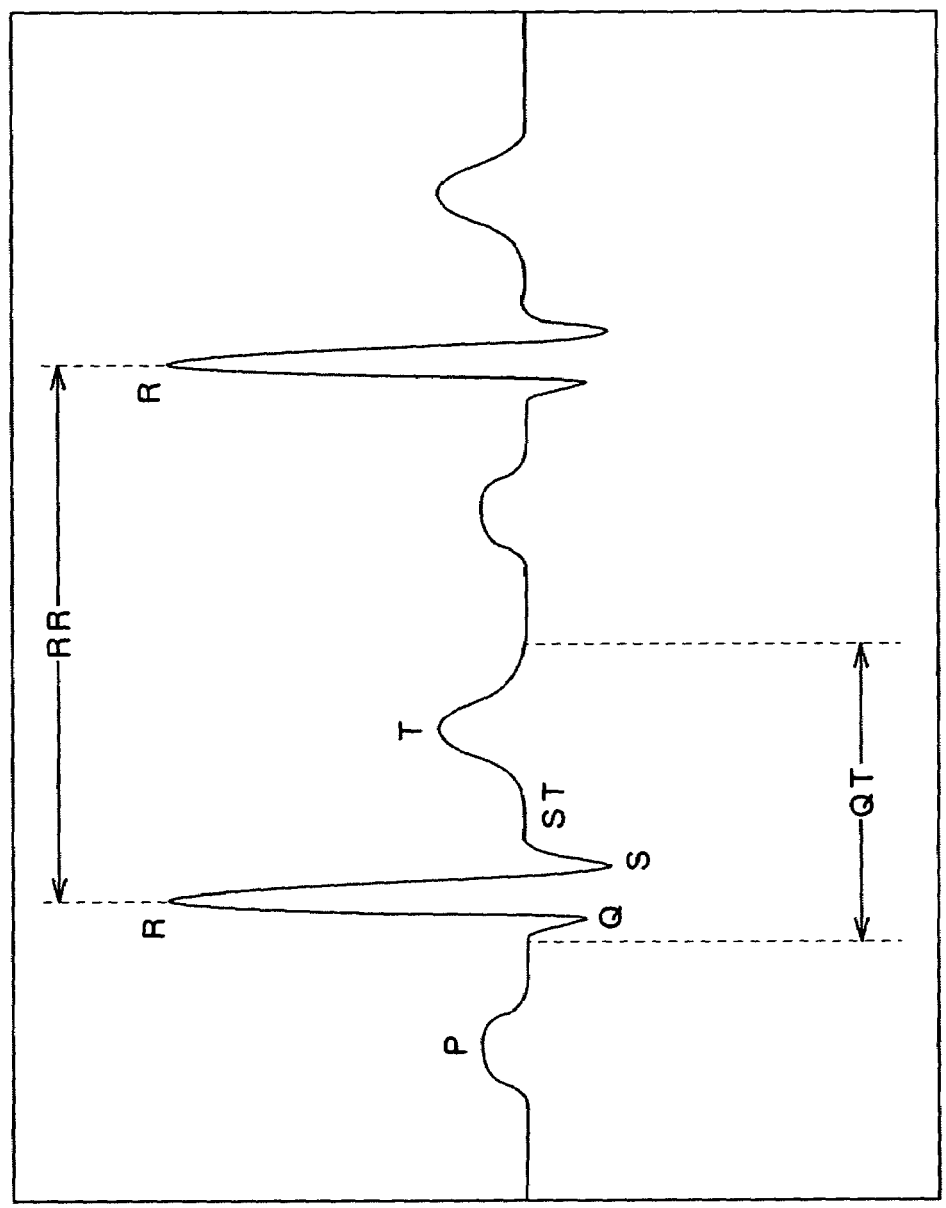
FIG. 5 schematically illustrates stored ECG wave data as a graph form according to an embodiment.

The CPU 10 continuously records digital data (electrocardiographic waveform data) obtained via the ECG electrodes 20 in the memory 17 (or the F-ROM 18) for each of the 12 leads. FIG. 5 is a graph schematically showing the ECG data (vertical axis: electric potential (voltage), horizontal axis: time) recorded for one of the leads. As shown in FIG. 5, the CPU 10 extracts identified value data R (R potential or R-wave height), T (T potential or T-wave height), Q (Q potential or Q-wave height), ST (ST level), QT (QT interval), and RR (RR interval) based on the recognition of P-wave, Q-wave, R-wave, S-wave, ST-segment, and T-wave, respectively, in the electrocardiogram and records them in the memory 17 (or the F-ROM 18). The CPU 10 recognizes a heartbeat and each wave in the electrocardiogram by the following process, for example, when the waveform is normal.

(1) Recognition of a Heartbeat: After sampling electrocardiographic waveform data (potential or voltage value) for a predetermined period of time, the CPU 10 recognizes an R-wave, which is a local maximum component exceeding a prescribed threshold, and the next R-wave (a local maximum component exceeding a prescribed threshold) and recognizes the RR interval as a heartbeat. At this time, T-wave components, which are local maximums other than the R-waves (having a frequency lower than that of R-waves) may be removed with a low-cut filter.

(2) P-wave: A local maximum which appears 200 to 300 msec (mili-second)before an R-wave is recognized as a P-wave.

(3) Q-wave: A local minimum which appears immediately before an R-wave is recognized as a Q-wave.

(4) S-wave: A local minimum which appears immediately after an R-wave is recognized as an S-wave.

(5) T-wave: A local maximum which appears between two R-waves is recognized as a T-wave.

(6) ST-segment: A linear interpolation is performed between an S-wave and a T-wave on the electrocardiogram, and the part which appears as a local maximum component between them is recognized as an ST-segment.

Noises with abnormal periods are generated and the extraction of identified values cannot be made precisely depending on the motion of the patient during the measurement of an electrocardiogram. As a method for removing such noises and obtaining precise identified value data, the technique disclosed in JP-A-Hei 6-261871, for example, may be used.

5-2. Vital Sign Circle Radar Creation Process

In this embodiment, an example in which the CPU 10 of the vital sign circle radar device 100 creates a vital sign circle radar based on an electrocardiogram and the $SpO_2$ value of a patient will be described. The vital sign circle radar creation process is performed per heartbeat. The electrocardiographic data sampling frequency is selected from, for example, 125, 250, 500 or 1000 Hz.

The vital sign circle radar creation process may be performed per a unit other than heartbeat or per predetermined unit time. The unit of the vital sign circle radar creation process and the electrocardiographic data sampling frequency may be changed by means known to those skilled in the art.

The vital sign circle radar creation process program in this embodiment will be described with reference to the flowchart in FIG. 6.

The CPU 10 of the vital sign circle radar device 100 performs a process of inputting a vital sign item selected by the user (step S601). The CPU 10 performs a process of inputting a scheduled measurement period (which corresponds to the "measurement period") selected by the user (step S603). The CPU 10 may output an interactive interface on the display screen 14 to receive the input of the vital sign item and the scheduled measurement period from the user. Alternatively, these items may be incorporated in the specifications of the vital sign circle radar device in advance. Here, the vital sign items "VPC, HR, QT and $SpO_2$ value" and a scheduled measurement period of "20 minutes" are previously set in the F-ROM 18 of the vital sign circle radar device 100.

The CPU 10 displays a circle radar on the display screen 14 based on the vital sign item inputted in step S601 and the scheduled measurement period inputted in step S603 (step S605). More specifically, a circle radar having an entire circle display period (which corresponds to the "entire display period") which is equal to the scheduled measurement period. Although the "entire circle display period" is equal to the scheduled measurement period in this embodiment, the present invention is not limited thereto. A period of time obtained by adding a predetermined period of time to the scheduled measurement period may be automatically set as the entire circle display period.

Then, the CPU 10 displays the vital sign name at the center of the circle radar (step S607). More specifically, when the vital sign item is $SpO_2$ value and the entire circle display period is 20 minutes, the CPU 10 displays a circle radar on the display screen 14 and "$SpO_2$" at the center of the circle radar (see a circle radar 53 in FIG. 4).

The CPU 10 performs a process of obtaining identified value data and the $SpO_2$ value (step S609 in FIG. 6). More specifically, the CPU 10 records the identified value data and the $SpO_2$ value in the memory 17 (or the F-ROM 18) via the ECG electrodes 20 and the blood oxygen saturation level measuring device 22. The CPU 10 determines whether identified value data corresponding to a heartbeat have been obtained (step S610). If not, the CPU 10 performs the process in step S609 again. The processes in and after step S611 in FIG. 6 are the same as the procedure of the vital sign circle radar creation program corresponding to one heartbeat. Thus, during the measurement of the biological information, the procedure of the vital sign circle radar creation program shown in and after step S611 in FIG. 6 is repeated at every heartbeat.

The CPU 10 performs an abnormality determination process based on the data (step S611). In this embodiment, an abnormality determination process is performed on the vital sign item selected from VPC, HR, QT, and $SpO_2$ value and inputted in step S601.

More specifically, the CPU 10 performs a subroutine of the abnormality determination process for the vital sign item selected in advance by the user in step S611. As the abnormality determination process, the CPU 10 performs a process shown in the flowchart in FIG. 7 when VPC has been selected, a process shown in the flowchart in FIG. 8 when HR has been selected, a process shown in the flowchart in FIG. 9 when QT has been selected, or a process shown in the flowchart in FIG. 10 when $SpO_2$ value has been selected. The abnormality determination processes will be described later.

The CPU 10 performs a process of displaying on the display screen 14 according to the result of the vital sign abnormality determination process.

The CPU 10 determines whether it is determined that the vital sign is abnormal by the vital sign abnormality determination process (step S613). When the vital sign is normal, the CPU 10 calculates an indication area in the vital sign circle radar for the vital sign (step S619) and displays green in the indication area (step S621) (see a normality indicator 62 in FIG. 4).

The calculation of the indication area is performed based on the measurement start time, the measurement time and the entire circle display period. More specifically, when "the measurement start time is 0:00, the measurement time is 0:10 and the entire circle display period is 20 minutes", for example, the indication area is about 180 degree away from the display start point of the circle radar.

If it is determined that the vital sign is abnormal in step S613, the CPU 10 calculates an indication area in the vital sign circle radar for the vital sign (step S615) and displays red in the indication area (step S617) (see an abnormality indicator 60 in FIG. 4). The calculation of the indication area is the same as above.

After the process in step S621 or S617, the CPU 10 determines whether the vital sign measurement process has been completed (step S623). If not, the processes in and after step S609 are repeated. If it is determined that the vital sign measurement process has been completed, the CPU 10 finishes the operation.

When there are a plurality of vital signs on which the CPU 10 has to perform an abnormality determination process, the processes in and after step S613 and before step S623 are performed on each vital sign and then the process in step S623 is performed.

5-3 Vital Sign Abnormality Determination Process

The abnormality determination process which the CPU 10 performs in step S611 in FIG. 6 will be described.

Figure 7:
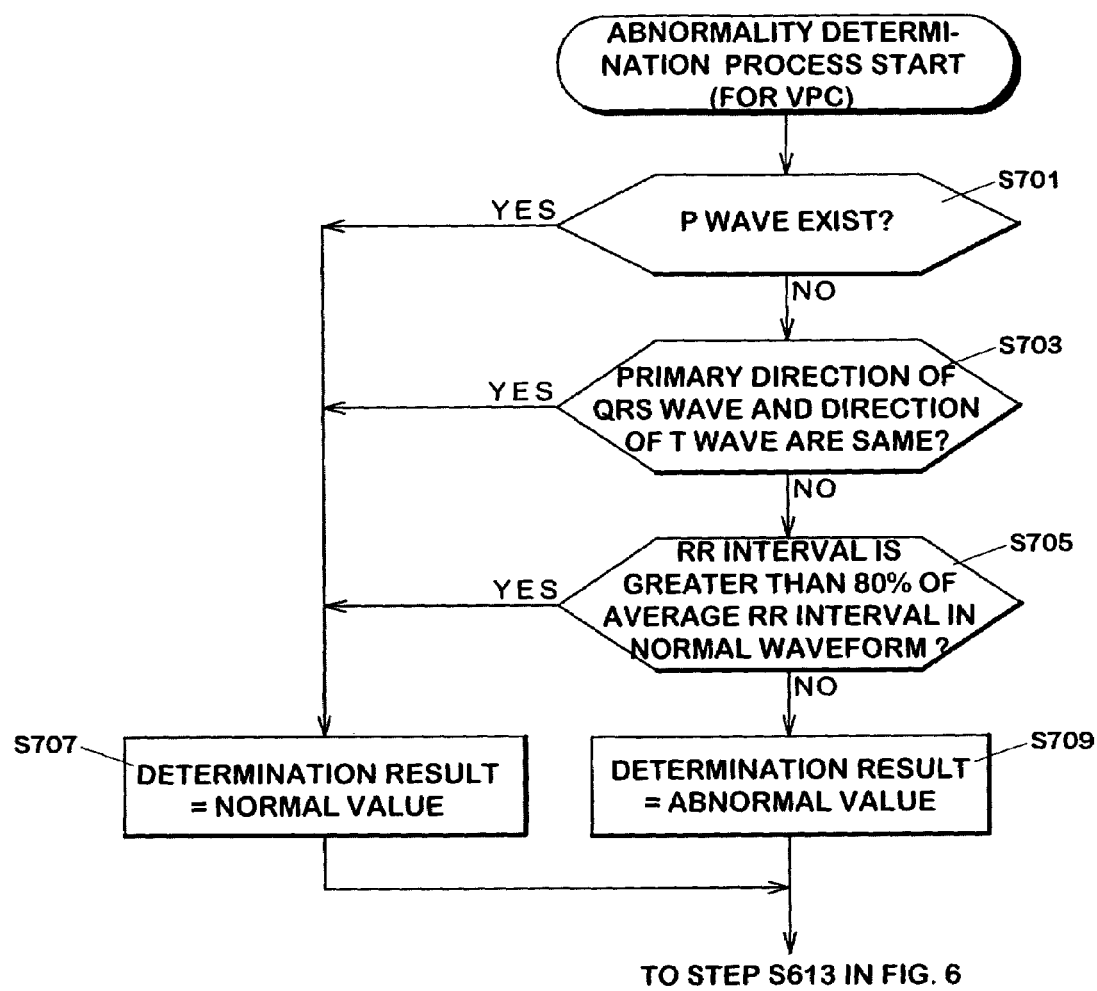
FIG. 7 illustrates a program flowchart for process that determines abnormality (i.e., for ventricular premature contraction (VPC)) according to an embodiment.
Figure 8:
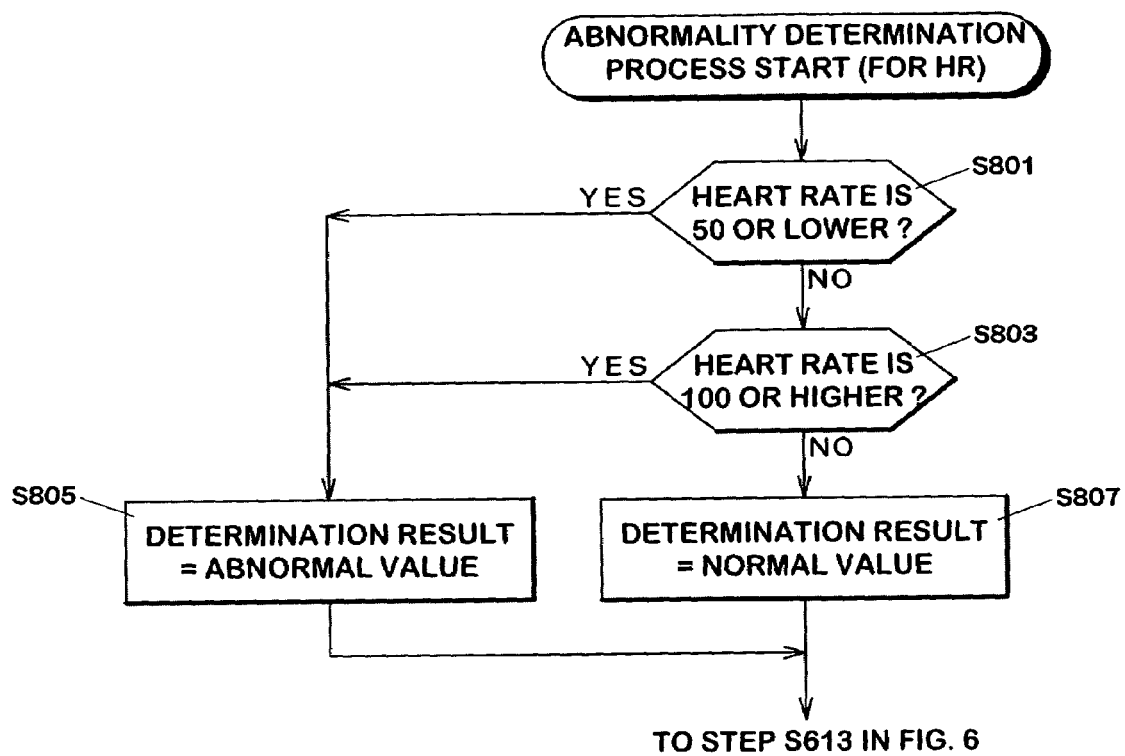
FIG. 8 illustrates a program flowchart for process that determines abnormality (i.e., for heart rate (HR)) according to an embodiment.
Figure 9:
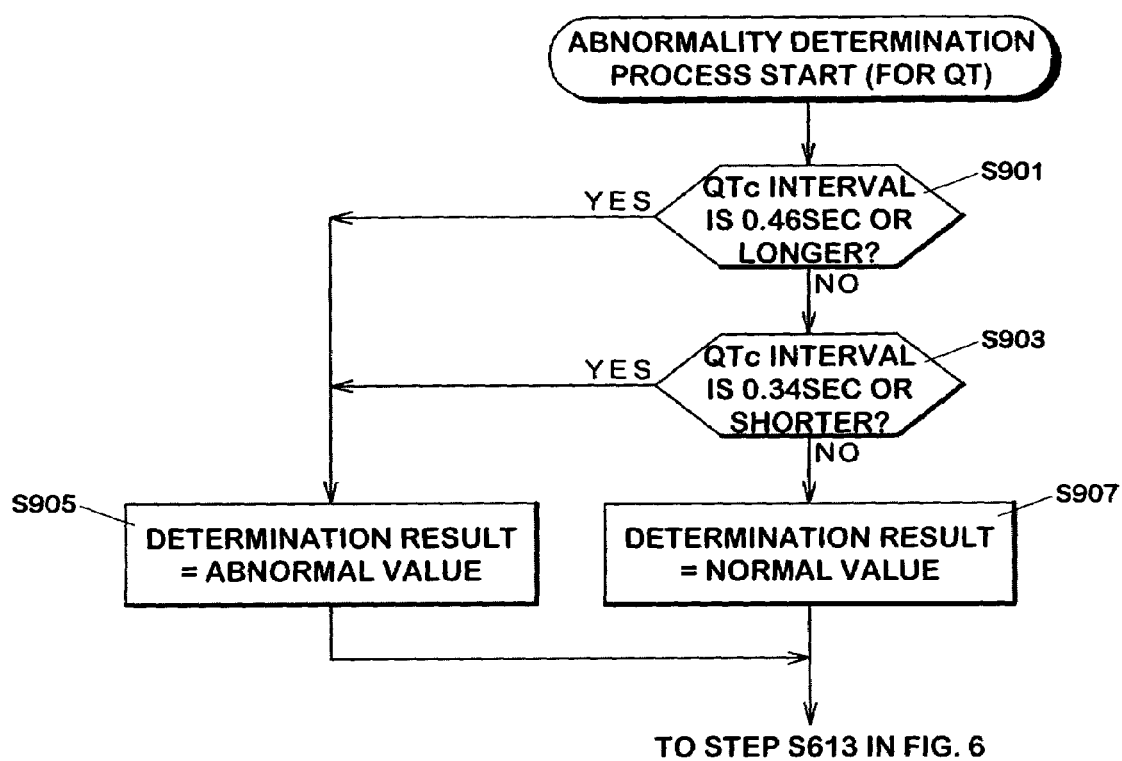
FIG. 9 illustrates a program flowchart for process that determines abnormality (i.e., for QT interval) according to an embodiment.
Figure 10:
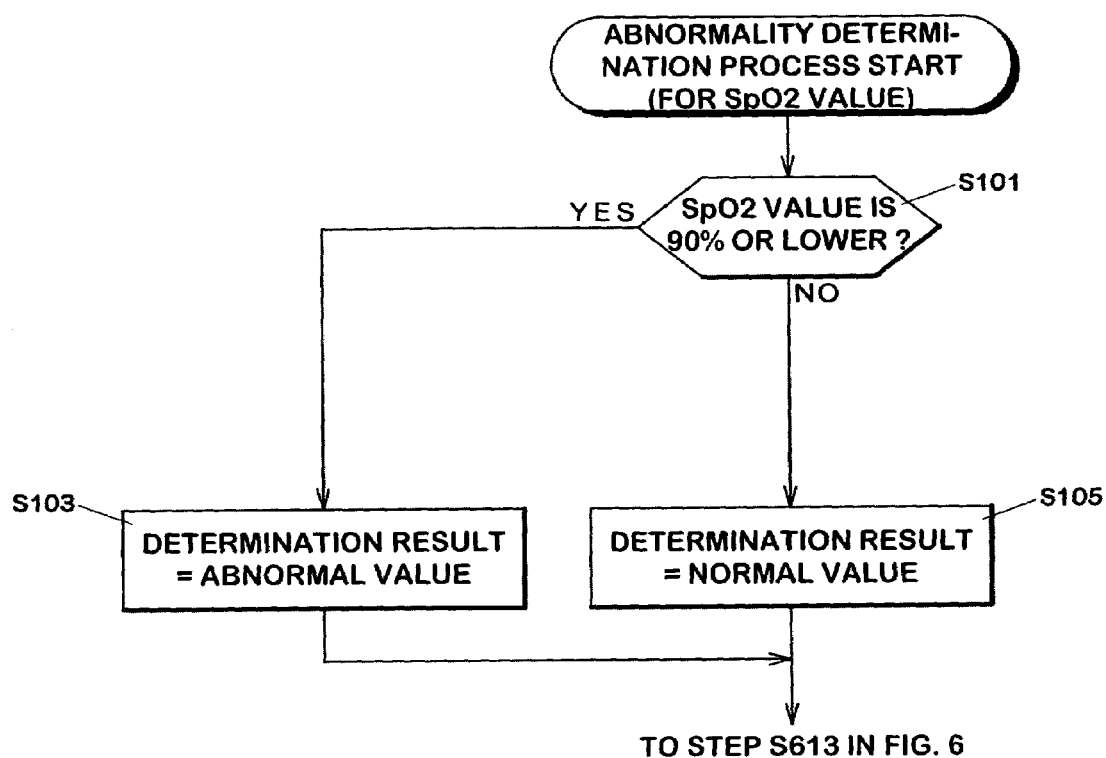
FIG. 10 illustrates a program flowchart for process that determines abnormality (i.e., for $SpO_2$ value) according to an embodiment.

As the abnormality determination process, the CPU 10 performs a process (vital sign abnormality determination process means) shown in the flowchart in FIG. 7 when VPC has been selected, a process shown in the flowchart in FIG. 8 when HR has been selected, a process shown in the flowchart in FIG. 9 when QT has been selected, or a process shown in the flowchart in FIG. 10 when $SpO_2$ value has been selected. In the abnormality determination processes described below, the CPU 10 uses identified value data and other data necessary for the abnormality determination (which will be described in the description of each abnormality determination process) recorded in the memory 17 (or the F-ROM 18).

(1) Abnormality Determination Process for VPC

FIG. 7 is a flowchart of the abnormality determination process for VPC.

In this embodiment, VPC (ventricular premature contraction) is determined as "abnormal" when the patient is having ventricular premature contractions and as "normal" when the patient having no ventricular premature contraction.

The CPU 10 of the vital sign circle radar device 100 determines whether there is a P-wave based on the identified value data recorded in the memory 17 (or the F-ROM 18) (step S701 in FIG. 7). More specifically, the CPU 10 determines whether there is a local maximum (P-wave) 200 to 300 msec before each R-wave in all the 12 leads. If there is a P-wave in at least one lead, the CPU 10 determines that "there is a P-wave."

If it is determined that there is a P-wave, the CPU 10 interprets the determination result as "normal" (step S707). If it is determined that there is no P-wave, the CPU 10 determines whether the primary directions of QRS-waves are the same as the direction of T-waves (step S703). More specifically, the CPU 10 determines that "the primary directions of QRS-waves are the same as the direction of T-waves" when the sign (plus or minus) of the R-potential (or R-wave height) value (mV, for example) is the same as that of the T-potential (or T-wave height) in at least six of the 12 leads.

If it is determined that the primary directions of QRS-waves are the same as the direction of T-waves, the CPU 10 performs the process in step S707. If it is determined that the primary directions of QRS-waves are not the same as the direction of T-waves, the CPU 10 determines whether the RR interval is greater than 80% of the average of RR intervals in a normal waveforms (step S705). More specifically, the CPU 10 determines that "the RR interval is greater than 80% of the average RR interval in a normal waveform" when the average of the RR-intervals (unit: msec, for example) in all the 12 leads in one heartbeat under examination is greater than 80% of the average of RR intervals (except those in abnormal waveforms) in all the 12 leads in the past five minutes.

If it is determined that the RR interval is greater than 80% of the average of RR intervals in normal waveforms, the CPU 10 performs the process in step S707. If it is determined that the RR interval is not greater than 80% of the average of RR intervals in normal waveforms, the CPU 10 interprets the determination result as "abnormal" (step S709).

Then, the CPU 10 performs the processes in and after step S613 in FIG. 6 based on the determination result obtained in the process in step S707 or step S709.

(2) Abnormality Determination Process for HR

FIG. 8 is a flowchart of the abnormality determination process for HR (heart rate). The HR is determined as "abnormal" when the heart rate is higher than a predetermined value or lower than a predetermined value and otherwise determined as "normal." The CPU 10 calculates the average of RR intervals (unit: sec, for example) in all the 12 leads in one heartbeat under examination and obtains heart rate data by dividing 60 by the average of the RR intervals.

The CPU 10 determines whether the heart rate is 50 (per minute) or lower (bradycardia) (step S801 in FIG. 8). If it is determined that the heart rate is 50 or lower, the CPU 10 interprets the determination result as "abnormal" (step S805). If it is determined that the heart rate is not 50 or lower, the CPU 10 determines whether the heart rate is 100 or higher (tachycardia) (step S803).

If it is determined that the heart rate is 100 or higher, the CPU 10 performs the process in step S805. If it is determined that the heart rate is not 100 or higher, the CPU 10 interprets the determination result as "normal" (step S807).

Then, the CPU 10 performs the processes in and after step S613 in FIG. 6 based on the determination result obtained in the process in step S805 or step S807.

(3) Abnormality Determination Process for QT

FIG. 9 is a flowchart of the abnormality determination process for QT (QT interval). In this embodiment, QT is determined as "abnormal" when a QTc value obtained by correcting a QT interval value is higher than a predetermined value or a lower than a predetermined value and otherwise as "normal." For example, the CPU 10 obtains the data of the average of QTc values in all the 12 leads in one heartbeat under examination as QT interval value (unit: msec, for example). A QT interval value is, for example, the interval between a Qb point obtained based on a Q-wave and a Te point obtained based on a T-wave on an electrocardiogram. The CPU 10 calculates a QTc value by dividing a QT interval value by $\sqrt{RR}$ (square root of the RR interval), for example.

The CPU 10 determines whether the QTc interval is 0.46 seconds or longer (step S901 in FIG. 9). If it is determined that the QTc interval is 0.46 seconds or longer (prolonged QT interval), the CPU 10 interprets the determination result as "abnormal" (step S905). If it is determined that the QTc interval is not longer than 0.46 seconds, the CPU 10 determines whether the QTc interval is 0.34 seconds or shorter (step S903).

If it is determined that the QTc interval is 0.34 seconds or shorter (shortened QT interval), the CPU 10 performs the process in step S905. If it is determined that the QTc interval is not 0.34 seconds or shorter, the CPU 10 interprets the determination result as "normal" (step S907).

Then, the CPU 10 performs the processes in and after step S613 in FIG. 6 based on the determination result obtained in the process in step S905 or S907.

(4) Abnormality Determination Process for the $SpO_2$ Value

FIG. 10 is a flowchart of the abnormality determination process for the $SpO_2$ value. In this embodiment, the $SpO_2$ value is determined as "abnormal" when it is lower than a predetermined value and otherwise as "normal." The CPU 10 performs the following determination using the $SpO_2$ value recorded in the memory 17 (or F-ROM 18).

The CPU 10 determines whether the $SpO_2$ value is 90% or lower (step S101 in FIG. 10). If it is determined that the $SpO_2$ value is 90% or lower, the CPU 10 interprets the determination result as "abnormal" (step S103). If it is determined that the $SpO_2$ value is not 90% or lower, the CPU 10 interprets the determination result as "normal" (step S105).

Then, the CPU 10 performs the processes in and after step S613 in FIG. 6 based on the determination result obtained in the process in step S103 or step S105.

5-3 Modification of Vital Sign Circle Radar Creation Process etc

The abnormality determination process for each of the vital signs shown as examples in this embodiment has been described. In the above embodiment, the abnormality determination process in step S613 in FIG. 6 is performed on all the vital sign items inputted in step S601 and the display process in and after step S613 is performed on every vital sign item. Then, when the display process is completed for every vital sign item, the vital sign circle radar creation process corresponding to one heartbeat is completed.

The algorithm of the vital sign circle radar creation process is not limited to the one described in the above embodiment and another algorithm may be employed. For example, an algorithm is used in which an abnormality determination process and a display process are sequentially performed on each vital sign item instead of an algorithm in which a display process is performed on every vital sign item after an abnormal determination process has been performed on every vital sign item.

Also, the algorithm of vital sign circle radar creation process, the algorithm of each of the abnormality determination processes, the colors to be displayed on the display screen 14 and so on described in the above embodiment are illustrative and may be changed by means known to those skilled in the art.

For example, the display process in steps S615, S617, S619 and S621 may be changed as follows.

This variation relates to saving time and energy in the display process. More specifically, the CPU 10 performs the processes in and after step S619, not every time the CPU 10 determines that the vital sign is normal in step S613 but when the determination that the vital sign is normal continues for five seconds or longer, for example. On the other hand, the CPU 10 performs the display process in and after step S615 every time it is determined that the vital sign is abnormal in step S613. According to the variation of the display process, it is possible to save time and energy in the display process when the vital sign is normal. The reference time (five seconds or longer) in the case where the vital sign is normal as described above is illustrative and may be changed depending on the length of the entire circle display period of the circle radar.

6. Effects of Embodiment

According to the above embodiment, the user of the vital sign circle radar device 100 can check and determine the status of the vital sign of the patient with ease.

In conventional vital sign display methods, a trend graph showing the changes in the value (parameter) of a biological signal within a predetermined period of time (the last one minute, for example) is displayed or the latest value of a biological signal is displayed at successive intervals. In such a case, it is difficult to check the history of abnormalities of the biological signal.

In this regard, according to the vital sign display method of the above embodiment, it is possible to check the history of the vital sign easily with a circle radar 50 (see FIG. 4) which can cover the length of time it takes to carry a patient on an ambulance (15 to 20 minutes in general). Thus, the user of the vital sign circle radar device 100 can visually recognize the information about when and how often the abnormalities of the biological signal occurred.

In the embodiment, the vital sign is displayed by the circle radar 50 and the like. Thus, the user can get the overall perspective of each vital sign without largely moving the line of sight, and can easily check the status of the vital sign within the measurement period.

Moreover, in this embodiment, since the vital sign is displayed by a vital sign circle radar by which it can be determined whether the vital sign is normal or abnormal, more information useful to diagnose the condition of the patient can be arranged in the display screen than when the original data of the vital sign is displayed (for example, when the changes in heart rate is shown in a graph). Also, a plurality of vital signs can be displayed simultaneously with ease.

As described above, the embodiment is characterized in that the value (parameter) of a biological signal is displayed in such a vital sign display style (radar) that it can be determined whether the vital sign is normal or abnormal. Thus, the user can grasp an abnormality of the living body (presence or absence of an abnormal value of a biological signal) promptly.

Also in the embodiment, since the vital sign is displayed in the form of a circle (circle, ring, or doughnut shape), the effect of giving a sense of security to the patient who sees the display screen can be expected.

7. Other Functions of the Vital Sign Circle Radar Device

In addition to the above-mentioned vital sign circle radar generating process, examples of optional functions of the vital sign circle radar device 100 will be described below.

7-1. Display of Heartbeat Condition

The vital sign circle radar device 100 displays a specific flashing symbol (or mark) in order to show a heartbeat condition (which corresponds to the term "means for outputting heartbeat-related information by varying display style"). More specifically, the CPU 10 processes a display of the flashing heart mark according to the heart rhythm measured, as illustrated in FIG. 4.

The user can confirm that the vital sign circle radar device 100 is running normally, and can also check the patient's heartbeat condition. In an alternative embodiment, the device outputs a specific sound (e.g. bleep sound) from the speaker 15 according to the heart rhythm, in conjunction with the flashing mark or instead of the flashing mark.

7-2. Warning for Impracticable Analysis

The vital sign circle radar device 100 displays a certain warning during the vital sign circle radar generating process when an ECG electrode 12 is detached from the patient or when trouble occurs in the generating process (which corresponds to the term "means for outputting warning signal when the vital sign analysis can not be executed"). More specifically, the CPU 10 displays a warning message stating "electrode detached" etc., on displaying area of "diagnostic information" on display 14.

The user who sees the warning can promptly understand that the vital sign circle radar generating process has been interrupted by the trouble. In alternative embodiments, in order to draw the user's attention to the display, the CPU 10 changes the color of the whole display or the color of part of the display, or outputs a warning sound (e.g. an alarm sound).

8. Other Embodiments

8-1 Modification of Vital Sign Display Style

Although FIG. 4 is shown as an example of the screen displayed by the vital sign circle radar device 100 in the above embodiment, the present invention is not limited thereto. As other embodiments of vital sign display style, the display styles shown in FIG. 11 may be employed. The outline of each display style will be described.

Figure 11A:
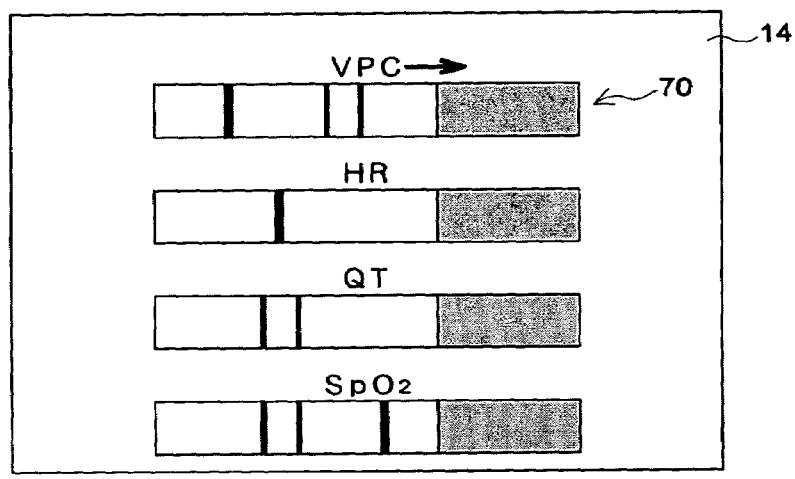
FIGS. 11A, 11B, and 11C illustrate other examples of a vital sign circle radar display.

FIG. 11A shows an example in which the vital signs are displayed with bar radars. In the drawing, a radar 70 for VPC and the like are displayed on the display screen 14. More specifically, indication points move from left to right on the screen as the measurement of the vital signs of the patient proceeds. The normal and abnormal conditions are indicated in the same manner as in the above embodiment. The entire display period of the bar radars is determined according to the measurement period selected by the user.

Figure 11B:
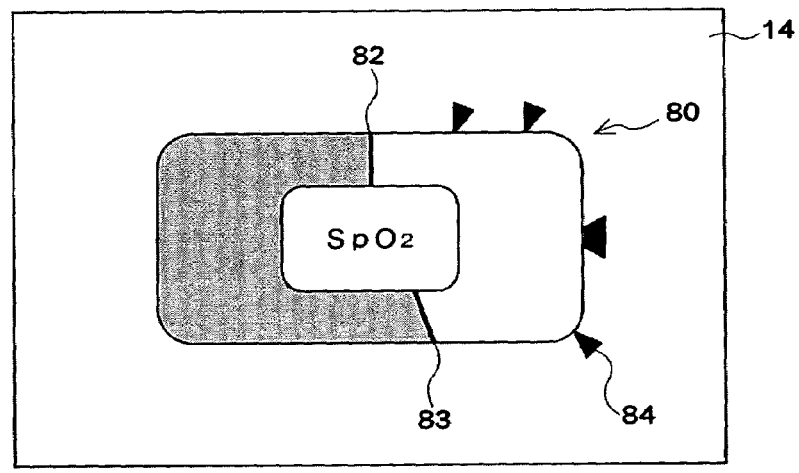

FIG. 11B shows an example in which a vital sign is displayed with a loop-shaped radar (ring-shaped radar or doughnut-shaped radar). In the drawing, a radar 80 for the $SpO_2$ value is displayed on the display screen 14. Unlike in the above embodiment, the current vital sign is displayed in a fixed position and the point indicating the measurement start time moves in this display style. More specifically, an indication point 83 indicating the measurement start time moves clockwise as the measurement proceeds while an indication point 82 indicating the current measurement time (the latest measurement time) is located at the upper center of the radar 80. Abnormality indication marks 84 as marks indicating abnormal conditions are displayed around the radar 80 so that the normal and abnormal conditions can be discriminated from each other.

Figure 11C:
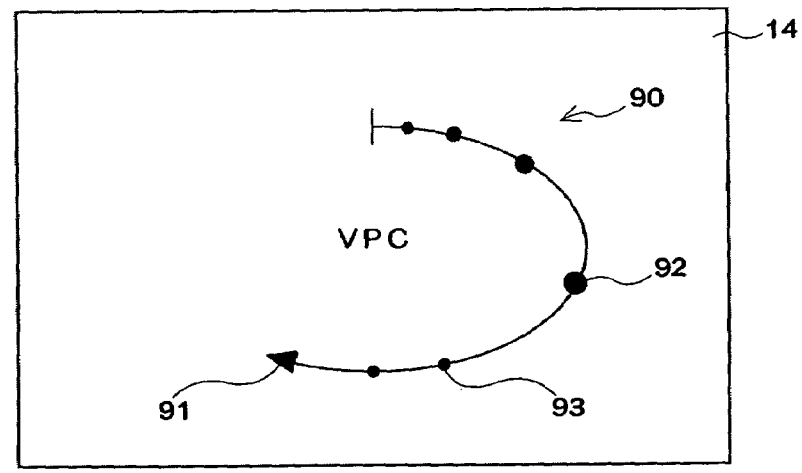

FIG. 11C shows an example in which a vital sign is displayed with a line. In the drawing, a line 90 for VPC is displayed on the display screen 14. More specifically, an indication point 91 moves clockwise from the upper center of the screen as the measurement of the vital sign of the patient proceeds. When the vital sign is abnormal, an abnormality indicator 92 or an abnormality indicator 93 indicating an abnormal condition is displayed on the line 90.

In the embodiments, as an example of the "vital sign displaying means", the process of displaying a vital sign on display 14 is illustrated. In alternative embodiments of the "vital sign display means (or "vital sign output means"), the vital sign can be outputted in computer-readable storage media such as memory card or CD-ROM. The vital sign can be outputted to connection means (e.g. telephone lines, wireless communication, the Internet, wire communication, infrared data communication, mobile phone, Bluetooth, PHS, or the like). The vital sign can be outputted as printed hard copy, facsimile, or the like.

The term of "vital sign displayed object" in the claims includes any output where a vital sign is visually recognizable. For example, a displayed object, a hard copy output, or a facsimile output of vital sign is included in the "vital sign displayed object".

8-2. Modification of Style of Displaying Abnormal Condition

Although the case where an indication point corresponding to an abnormal condition is displayed in red (see abnormality indicator 60 in FIG. 4) is described as an example of the style of displaying a vital sign when the living body is in an abnormal condition (the biological signal shows an abnormal value) in the above embodiment, the present invention is not limited thereto. The following displaying method may be employed as another embodiment of the style of displaying an abnormal condition.

A first variation of the style of displaying an abnormal condition is to blink the indication point indicating an abnormal condition. More specifically, the abnormality indicator 60 shown in FIG. 4 is blinked in red and the like.

A second variation of the style of displaying an abnormal condition is to change the display style depending on to the level of the abnormal value. More specifically, the degree of abnormality (including the severity or seriousness) is classified in levels (ranked) and the color (saturation, lightness or hue, for example) of the indication point is changed depending on the level. The following chart is an example of classification of levels of abnormality of heart rate (HR).

$HR<30 \rightarrow$ Abnormal level=−2 (bradycardia)
$30 \leq HR<50 \rightarrow$ Abnormal level=−1 (bradycardia)
$50 \leq HR<120 \rightarrow$ Abnormal level=0 (normal)
$120<HR \leq 180 \rightarrow$ Abnormal level=1 (tachycardia)
$180<HR \rightarrow$ Abnormal level=2 (tachycardia)

When the color saturation of the "red" of the abnormality indicator 60 (see FIG. 4) is increased, for example based on the levels of abnormality when the abnormality level is high (a function of a "vital sign abnormality level indicator means"), it is possible to provide detailed information about the abnormality to the user.

The method of changing the style of displaying depending on the level of abnormality is not limited to the above example. For example, the size of the indicating points may be changed. For example, as shown in FIG. 11C, the abnormality indicator 93 is displayed when the abnormality level is low, and the abnormality indicator 92, which is larger in size, is displayed when the abnormality level is high.

8-3. Embodiments of Device Configuration

In the embodiments, the vital sign circle radar device 100 executes both ECG measurement and vital sign circle radar display. In alternative embodiments, those functions can be separately executed by two or more discrete devices. For example, one device can execute an ECG measurement and ECG data output, and the other device (which corresponds to "vital sign display device") can execute a vital sign circle radar display based on the ECG data input.

The configuration of the devices (the number and combination of devices) for performing the process of measuring an electrocardiogram, the process of measuring the $SpO_2$ value, the abnormality determination process and the vital sign display process, respectively, and the configuration of the CPU may be changed by means known to those skilled in the art.

For example, although the CPU 10 of the vital sign circle radar device 100 performs the abnormality determination for the $SpO_2$ value according to the flowchart shown in FIG. 10 in the above embodiment, the present invention is not limited thereto. The CPU in the blood oxygen saturation level measuring device 22 may perform the abnormality determination and transmit the result of the determination (which corresponds to a "signal generated based on a biological signal," which includes a normality signal and an abnormality signal, or a normality signal or an abnormality signal, for example) to the CPU 10.

Although the vital sign is displayed based on electrocardiographic data and the $SpO_2$ value in the above embodiment, the present invention is not limited thereto. Auxiliary devices other that the blood oxygen saturation level measuring device 22 may be connected to the vital sign circle radar device 100 as another embodiment. More specifically, a blood pressure measuring device may be connected to the vital sign circle radar device 100 as an auxiliary device and "blood pressure" (BP) may be displayed as the vital sign.

8-4. Application Embodiments of Vital Sign Circle Radar Device

In the embodiments, the vital sign circle radar device 100 is used in ambulances. In alternative embodiments, the device can be used in any emergency medical arena in a portable form, used for home medical care by setting the device in a home, or used for living bodies including human or animals.

Devices that have similar functions with that of the vital sign circle radar device 100 can be installed in the driver's seat of an automobile or an electric train, an airplane cockpit, or the like, in order to prevent a serious accident from occurring when the driver develops a heart attack due to myocardial infarction etc. In other embodiments, such devices can be installed on a toilet seat, etc., for daily health care. For those applications, it is advantageous for the ECG electrodes 20 to be installed in an area with which the subject's body necessarily makes contact, such as a handle, toilet seat, handrail, or the like.

8-5. Program Execution

In the embodiments, the computer program for the CPU 10 is stored in the F-ROM 18. The computer program can be installed on the hard disk etc. from an installation CD-ROM (not shown). In alternative embodiments, the program can be installed from computer-readable storage media such DVD-ROM, a flexible disk (FD) or IC card (not shown). Alternatively, the program can be downloaded to the devices via the communications lines. The program storied on CD-ROM may also be directly executed although the program stored on CD-ROM can be executed indirectly by installing the program.

Computer-executable programs used in the embodiments include a program to be executable just after installation, a program that needs to be converted to another format (e.g. decompressing compressed data), or a program to be executable within a module.

A general description of the present invention as well as preferred embodiments of the invention has been set forth above. It is to be expressly understood, however, that the terms described above are for purpose of illustration only and are not intended as definitions of the limits of the invention. Those skilled in the art to which the present invention pertains will recognize and be able to practice other variations in the system, device, and methods described which fall within the teachings of this invention. Accordingly, all such modifications are deemed to be within the scope of the invention.

What is claimed is:

1. A vital sign display device for displaying a vital sign, comprising:

means for obtaining a biological signal;

means for determining whether a living body condition represented by the biological signal is abnormal or not, which is based on the obtained biological signal; and means for displaying a vital sign obtained from the biological signal, the vital sign showing determination results from the determining means, wherein the vital sign shows in a circular shaped time series configuration whether the living body condition represented by the biological signal is abnormal or not.

2. The device according to claim 1, wherein the vital sign is displayed so as to follow a circular shape according to the time series of the vital sign.

3. The device according to claim 1, further comprising means for selecting display styles, wherein an entire display period corresponding to a scheduled measurement period.

4. The device according to claim 1, further comprising means for displaying an item name of vital sign, wherein the vital sign item name displaying means displays the item name by relating the item name to the displayed vital sign.

5. The device according to claim 1, wherein a display style of vital sign is changed to another style when the abnormal condition occurs.

6. The device according to claim 1, wherein the vital sign is at least one of VPC (ventricular premature contraction), HR (heart rate), QT interval, and $SpO_2$ value (oxygen saturation in blood).

7. A vital sign display device in accordance with claim 1, wherein the circular shape is a shape around which one can make a circuit.

8. A vital sign display device in accordance with claim 1, wherein the circular shape is one selected from a loop shape, ring shape, circle shape, round shape, oval shape, doughnut shape, annular shape and polygonal shape formed by straight lines, curves or a combination of straight lines and curves.

9. A computer readable medium having stored thereon a computer program for a vital sign display device that displays a vital sign, wherein the program is implemented in a computer and capable of causing the computer to perform:
 means for obtaining a biological signal;
 means for determining whether a living body condition represented by the biological signal is abnormal or not, which is based on the obtained biological signal; and
 means for displaying a vital sign obtained from the biological signal, the vital sign showing determination results from the determining means, wherein the vital sign shows in a circular shaped time series configuration whether the living body condition represented by the biological signal is abnormal or riot.

10. A computer readable medium in accordance with claim 9, wherein the circular shape is a shape around which one can make a circuit.

11. A computer readable medium accordance with claim 9, wherein the circular shape is one selected from a loop shape, ring shape, circle shape, round shape, oval shape, doughnut shape, annular shape and polygonal shape formed by straight lines, curves or a combination of straight lines and curves.

12. Means for displaying a vital sign, comprising:
 means for obtaining a biological signal or a signal generated from the biological signal; and
 means for displaying a vital sign, obtained from the biological signal or the signal generated from the biological signal, wherein the vital sign shows in a circular shaped time series configuration whether the living body condition represented by the biological signal is abnormal or not.

13. A vital sign display device in accordance with claim 12, wherein the circular shape is a shape around which one can make a circuit.

14. A vital sign display device in accordance with claim 12, wherein the circular shape is one selected from a loop shape, ring shape, circle shape, round shape, oval shape, doughnut shape, annular shape and polygonal shape formed by straight lines, curves or a combination of straight lines and curves.

15. A vital sign display device for displaying a vital sign, comprising:
 means for obtaining a biological signal;
 means for determining whether a living body condition represented by the biological signal is abnormal or not, which is based on the obtained biological signal; and
 means for displaying a vital sign obtained from the biological signal, the vital sign showing in a circular shaped time series configuration whether the living body condition represented by the biological signal is abnormal or not, wherein the display is executed by moving a display object in the direction to draw a circular shape according to time series of the vital sign.

16. A vital sign display device in accordance with claim 15, wherein the circular shape is a shape around which one can make a circuit.

17. A vital sign display device in accordance with claim 15, wherein the circular shape is one selected from a loop shape, ring shape, circle shape, round shape, oval shape, doughnut shape, annular shape and polygonal shape formed by straight lines, curves or a combination of straight lines and curves.

18. In vital sign display device, a method for displaying a vital sign, comprising:
 obtaining a biological signal;
 determining whether a living body condition represented by the biological signal is abnormal or not, which is based on the obtained biological signal; and
 instructing to display a vital sign obtained from the biological signal, the vital sign showing in a circular shaped time series configuration whether the living body condition represented by the biological signal is abnormal or not, wherein the vital sign is arranged in time series that illustrates a history of the vital sign.

19. A method for displaying a vital sign in accordance with claim 18, wherein the circular shape is a shape around which one can make a circuit.

20. A method for displaying a vital sign in accordance with claim 18, wherein the circular shape is one selected from a loop shape, ring shape, circle shape, round shape, oval shape, doughnut shape, annular shape and polygonal shape formed by straight lines, curves or a combination of straight lines and curves.

21. In vital sign display device, a method for displaying a vital sign, comprising:
 instructing to display a vital sign, obtained from a biological signal or a signal generated from the biological signal, the vital sign showing in a circular shaped time series configuration whether the living body condition represented by the biological signal is abnormal or not, wherein the vital sign is arranged in time series that illustrates a history of the vital sign.

22. A method for displaying a vital sign in accordance with claim 21, wherein the circular shape is a shape around which one can make a circuit.

23. A method for displaying a vital sign in accordance with claim 21, wherein the circular shape is one selected from a loop shape, ring shape, circle shape, round shape, oval shape, doughnut shape, annular shape and polygonal shape formed by straight lines, curves or a combination of straight lines and curves.

24. In vital sign display device, a method for displaying a vital sign, comprising:
 obtaining a biological signal;
 determining whether living body condition represented by the biological signal is abnormal or not, which is based on the obtained biological signal; and
 instructing to display a vital sign obtained from the biological signal, the vital sign showing in a circular shaped time series configuration whether the living body condition represented by the biological signal is abnormal or not.

25. A method for displaying a vital sign in accordance with claim 24, wherein the circular shape is a shape around which one can make a circuit.

26. A method for displaying a vital sign in accordance with claim 24, wherein the circular shape is one selected from a loop shape, ring shape, circle shape, round shape, oval shape, doughnut shape, annular shape and polygonal shape formed by straight lines, curves or a combination of straight lines and curves.

27. A method for displaying a vital sign comprising the steps of:
 obtaining a biological signal;
 determining whether a living body condition represented by the biological signal is abnormal or not, which is based on the obtained biological signal; and
 displaying a vital sign obtained from the biological signal, the vital sign showing in a circular shaped time series configuration whether the living body condition represented by the biological signal is abnormal or not, wherein the vital sign is arranged in time series that illustrates a history of the vital sign.

28. A method for displaying a vital sign in accordance with claim 27, wherein the circular shape is a shape around which one can make a circuit.

29. A method for displaying a vital sign in accordance with claim 27, wherein the circular shape is one selected from a loop shape, ring shape, circle shape, round shape, oval shape, doughnut shape, annular shape and polygonal shape formed by straight lines, curves or a combination of straight lines and curves.

30. A method for displaying a vital sign comprising the steps of:
   obtaining a biological signal;
   determining whether living body condition represented by the biological signal is abnormal or not, which is based on the obtained biological signal; and
   displaying a vital sign obtained from the biological signal, the vital sign showing in a circular shaped time series configuration whether the living body condition represented by the biological signal is abnormal or not wherein the display is executed by moving a display object in the direction of following a circular shape according to time series of the vital sign.

31. A method for displaying a vital sign in accordance with claim 30, wherein the circular shape is a shape around which one can make a circuit.

32. A method for displaying a vital sign in accordance with claim 30, wherein the circular shape is one selected from a loop shape, ring shape, circle shape, round shape, oval shape, doughnut shape, annular shape and polygonal shape formed by straight lines, curves or a combination of straight lines and curves.

33. A vital sign display device comprising:
   a communication interface that receives a biological signal;
   a processor adapted to determine, based on the obtained biological signal, whether a body condition represented by the biological signal is abnormal; and
   a display system that displays in a historical time series a status of the vital sign based on the biological signal, the vital sign showing in a circular shaped time series configuration whether the living body condition represented by the biological signal is abnormal or not.

34. A vital sign display device in accordance with claim 33, wherein the circular shape is a shape around which one can make a circuit.

35. A vital sign display device in accordance with claim 33, wherein the circular shape is one selected from a loop shape, ring shape, circle shape, round shape, oval shape, doughnut shape, annular shape and polygonal shape formed by straight lines, curves or a combination of straight lines and curves.

* * * * *